United States Patent
Dugan

(10) Patent No.: US 9,566,373 B2
(45) Date of Patent: Feb. 14, 2017

(54) ANTI-PROLIFERATIVE AND ANTI-INFLAMMATORY AGENT COMBINATION FOR TREATMENT OF VASCULAR DISORDERS WITH AN IMPLANTABLE MEDICAL DEVICE

(71) Applicant: Abbott Cardiovascular Systems Inc., Santa Clara, CA (US)

(72) Inventor: Stephen Dugan, San Francisco, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 14/829,558

(22) Filed: Aug. 18, 2015

(65) Prior Publication Data

US 2016/0045646 A1 Feb. 18, 2016

Related U.S. Application Data

(60) Division of application No. 14/192,705, filed on Feb. 27, 2014, now Pat. No. 9,138,337, which is a division
(Continued)

(51) Int. Cl.
*A61K 9/52* (2006.01)
*A61L 31/16* (2006.01)
(Continued)

(52) U.S. Cl.
CPC ............... *A61L 31/16* (2013.01); *A61F 2/91* (2013.01); *A61K 9/0024* (2013.01); *A61K 9/1647* (2013.01); *A61K 31/436* (2013.01); *A61K 31/4745* (2013.01); *A61K 31/573* (2013.01); *A61L 27/54* (2013.01); *A61L 27/58* (2013.01); *A61L 31/10* (2013.01); *A61L 31/148* (2013.01);
(Continued)

(58) Field of Classification Search
CPC ..... A61K 9/0024; A61K 9/1647; A61L 27/54; A61L 27/58
See application file for complete search history.

(56) References Cited

U.S. PATENT DOCUMENTS 3,640,741 A 2/1972 Etes
3,865,108 A 2/1975 Hartop
(Continued)

FOREIGN PATENT DOCUMENTS

EP 2 578 186 4/2003
EP 1440699 7/2004
(Continued)

OTHER PUBLICATIONS

Guidant Press Releases Mar. 27, 2002, "Guidant licenses Everolimus from Novartis for Drug Eluting Stents," Boston Scientific, Jun. 23, 2015, pp. 1-3.
(Continued)

*Primary Examiner* — Carlos Azpuru
(74) *Attorney, Agent, or Firm* — Squire Patton Boggs (US) LLP

(57) ABSTRACT

Drug-delivery systems such as drug-delivery stents having an anti-proliferative agent such as everolimus and an anti-flammatory agent such as clobetasol are provided. Also disclosed are methods of treating a vascular impairment such as restenosis or vulnerable plaque.

9 Claims, 6 Drawing Sheets

Related U.S. Application Data of application No. 12/838,329, filed on Jul. 16, 2010, now Pat. No. 8,709,469, which is a continuation-in-part of application No. 11/090,507, filed on Mar. 24, 2005, now Pat. No. 7,758,881, which is a continuation-in-part of application No. 10/882,506, filed on Jun. 30, 2004, now abandoned.

(51) Int. Cl.
| | | |
|---|---|---|
| *A61K 9/00* | (2006.01) | |
| *A61K 9/16* | (2006.01) | |
| *A61L 27/54* | (2006.01) | |
| *A61L 27/58* | (2006.01) | |
| *A61F 2/91* | (2013.01) | |
| *A61K 31/4745* | (2006.01) | |
| *A61K 31/573* | (2006.01) | |
| *A61K 31/436* | (2006.01) | |
| *A61L 31/10* | (2006.01) | |
| *A61L 31/14* | (2006.01) | |

(52) U.S. Cl.
CPC ...... *A61F 2250/0067* (2013.01); *A61F 2250/0068* (2013.01); *A61L 2300/204* (2013.01); *A61L 2300/216* (2013.01); *A61L 2300/41* (2013.01); *A61L 2300/416* (2013.01); *A61L 2300/604* (2013.01)

(56) References Cited

U.S. PATENT DOCUMENTS

| | | |
|---|---|---|
| 3,992,562 A | 11/1976 | Denzinger et al. |
| 4,002,173 A | 1/1977 | Manning et al. |
| 4,014,335 A | 3/1977 | Arnold |
| 4,207,893 A | 6/1980 | Michaels |
| 5,540,931 A | 7/1996 | Hewitt et al. |
| 5,605,696 A | 2/1997 | Eury et al. |
| 5,646,160 A | 7/1997 | Morris et al. |
| 5,649,977 A | 7/1997 | Campbell |
| 5,670,161 A | 9/1997 | Healy et al. |
| 5,756,553 A | 5/1998 | Iguchi et al. |
| 5,770,609 A | 6/1998 | Grainger et al. |
| 5,788,979 A | 8/1998 | Alt et al. |
| 5,820,917 A | 10/1998 | Tuch |
| 5,824,048 A | 10/1998 | Tuch |
| 5,843,172 A | 12/1998 | Yan |
| 5,857,998 A | 1/1999 | Barry |
| 5,858,746 A | 1/1999 | Hubbell et al. |
| 5,871,437 A | 2/1999 | Alt |
| 5,972,027 A | 10/1999 | Johnson |
| 6,153,252 A | 11/2000 | Hossainy et al. |
| 6,156,373 A | 12/2000 | Zhong et al. |
| 6,204,245 B1 | 3/2001 | Siegel et al. |
| 6,239,124 B1 | 5/2001 | Zenke et al. |
| 6,335,029 B1 | 1/2002 | Kamath et al. |
| 6,368,658 B1 | 4/2002 | Schwarz et al. |
| 6,490,228 B2 | 12/2002 | Killam |
| 6,527,801 B1 | 3/2003 | Dutta |
| 6,565,659 B1 | 5/2003 | Pacetti et al. |
| 6,585,764 B2 | 7/2003 | Wright et al. |
| 6,613,807 B2 | 9/2003 | Uhrich |
| 6,685,928 B2 | 2/2004 | Uhrich et al. |
| 6,713,119 B2 | 3/2004 | Hossainy et al. |
| 6,790,228 B2 | 9/2004 | Hossainy et al. |
| 6,861,088 B2 | 3/2005 | Weber et al. |
| 6,865,810 B2 | 3/2005 | Stinson |
| 6,869,443 B2 | 3/2005 | Buscemi et al. |
| 6,878,160 B2 | 4/2005 | Gilligan et al. |
| 6,887,270 B2 | 5/2005 | Miller et al. |
| 6,887,485 B2 | 5/2005 | Fitzhugh et al. |
| 6,890,546 B2 | 5/2005 | Mollison et al. |
| 6,899,729 B1 | 5/2005 | Cox et al. |
| 6,899,731 B2 | 5/2005 | Li et al. |
| 6,908,624 B2 | 6/2005 | Hossainy et al. |
| 6,939,376 B2 | 9/2005 | Shulze et al. |
| 7,122,615 B1 | 10/2006 | Uhrich |
| 7,195,640 B2 | 3/2007 | Falotico et al. |
| 7,202,325 B2 | 4/2007 | Pacetti et al. |
| 7,214,759 B2 | 5/2007 | Pacetti et al. |
| 7,217,286 B2 | 5/2007 | Falotico et al. |
| 7,285,304 B1 | 10/2007 | Hossainy et al. |
| 7,378,105 B2 | 5/2008 | Burke et al. |
| 7,378,106 B2 | 5/2008 | Hossainy et al. |
| 7,390,333 B2 | 6/2008 | Dutta |
| 7,399,480 B2 | 7/2008 | Mollison et al. |
| 7,419,678 B2 | 9/2008 | Falotico et al. |
| 7,445,792 B2 | 11/2008 | Toner et al. |
| 7,563,483 B2 | 7/2009 | Hossainy et al. |
| 7,569,655 B2 | 8/2009 | Pacetti et al. |
| 7,674,285 B2 | 3/2010 | Varshney et al. |
| 7,682,387 B2 | 3/2010 | Shulze et al. |
| 7,682,647 B2 | 3/2010 | Hossainy et al. |
| 7,727,275 B2 | 6/2010 | Betts et al. |
| 7,758,881 B2 | 7/2010 | Dugan |
| 7,776,991 B2 | 8/2010 | Pacetti et al. |
| 7,820,190 B2 | 10/2010 | Hossainy et al. |
| 7,875,283 B2 | 1/2011 | Hossainy et al. |
| 8,092,822 B2 | 1/2012 | Pacetti et al. |
| 8,109,994 B2 | 2/2012 | Dutta |
| 8,232,322 B2 | 7/2012 | East et al. |
| 8,252,046 B2 | 8/2012 | Shulze et al. |
| 8,308,795 B2 | 11/2012 | Shulze et al. |
| 8,545,550 B2 | 10/2013 | Shulze et al. |
| 8,715,341 B2 | 5/2014 | Shulze et al. |
| 8,952,123 B1 | 2/2015 | Ding |
| 9,205,051 B2 * | 12/2015 | Canham ............... A61K 9/0019 |
| 2001/0029398 A1 | 10/2001 | Jadhav |
| 2002/0005206 A1 | 1/2002 | Falotico et al. |
| 2002/0016625 A1 | 2/2002 | Falotico et al. |
| 2002/0133183 A1 | 9/2002 | Lentz et al. |
| 2002/0188277 A1 | 12/2002 | Roorda et al. |
| 2003/0039689 A1 | 2/2003 | Chen et al. |
| 2003/0060877 A1 | 3/2003 | Falotico et al. |
| 2003/0088307 A1 | 5/2003 | Shulze et al. |
| 2003/0108588 A1 | 6/2003 | Chen et al. |
| 2003/0203915 A1 | 10/2003 | Fang et al. |
| 2003/0203991 A1 | 10/2003 | Schottman et al. |
| 2003/0225450 A1 | 12/2003 | Shulze et al. |
| 2004/0024450 A1 | 2/2004 | Shulze et al. |
| 2004/0086542 A1 | 5/2004 | Hossainy et al. |
| 2004/0143322 A1 | 7/2004 | Litvack et al. |
| 2004/0162609 A1 | 8/2004 | Hossainy et al. |
| 2005/0004663 A1 | 1/2005 | Llanos et al. |
| 2005/0021131 A1 | 1/2005 | Venkatraman et al. |
| 2005/0033412 A1 | 2/2005 | Wu et al. |
| 2005/0037052 A1 | 2/2005 | Udipi et al. |
| 2005/0038134 A1 | 2/2005 | Loomis et al. |
| 2005/0038497 A1 | 2/2005 | Neuendorf et al. |
| 2005/0043786 A1 | 2/2005 | Chu et al. |
| 2005/0049693 A1 | 3/2005 | Walker |
| 2005/0049694 A1 | 3/2005 | Neary |
| 2005/0054774 A1 | 3/2005 | Kangas |
| 2005/0055044 A1 | 3/2005 | Kangas |
| 2005/0055078 A1 | 3/2005 | Campbell |
| 2005/0060020 A1 | 3/2005 | Jenson |
| 2005/0064088 A1 | 3/2005 | Fredrickson |
| 2005/0065501 A1 | 3/2005 | Wallace |
| 2005/0065545 A1 | 3/2005 | Wallace |
| 2005/0065593 A1 | 3/2005 | Chu et al. |
| 2005/0074406 A1 | 4/2005 | Couvillon, Jr. et al. |
| 2005/0074545 A1 | 4/2005 | Thomas |
| 2005/0075714 A1 | 4/2005 | Cheng et al. |
| 2005/0079274 A1 | 4/2005 | Palasis et al. |
| 2005/0084515 A1 | 4/2005 | Udipi et al. |
| 2005/0106210 A1 | 5/2005 | Ding et al. |
| 2005/0113903 A1 | 5/2005 | Rosenthal et al. |
| 2005/0176678 A1 | 8/2005 | Horres et al. |
| 2005/0182390 A1 | 8/2005 | Shanley |
| 2005/0238686 A1 | 10/2005 | Hossainy et al. |
| 2006/0002968 A1 | 1/2006 | Stewart et al. |
| 2006/0014720 A1 | 1/2006 | Hossainy et al. |
| 2006/0034888 A1 | 2/2006 | Pacetti et al. |
| 2006/0105019 A1 | 5/2006 | Stewart et al. |

(56) References Cited

U.S. PATENT DOCUMENTS

| | | |
|---|---|---|
| 2006/0198867 A1 | 9/2006 | Toner et al. |
| 2006/0269586 A1 | 11/2006 | Pacetti |
| 2006/0280770 A1 | 12/2006 | Hossainy et al. |
| 2007/0093617 A1 | 4/2007 | DesNoyer et al. |
| 2007/0149724 A1 | 6/2007 | Pacetti et al. |
| 2007/0167602 A1 | 7/2007 | Pacetti et al. |
| 2007/0224240 A1 | 9/2007 | Toner et al. |
| 2007/0228345 A1 | 10/2007 | Pacetti |
| 2007/0254012 A1 | 11/2007 | Ludwig et al. |
| 2008/0004694 A1 | 1/2008 | Mack et al. |
| 2008/0014170 A1 | 1/2008 | Hnojewyj et al. |
| 2008/0153790 A1 | 6/2008 | Mollison et al. |
| 2008/0175884 A1 | 7/2008 | Mollison et al. |
| 2009/0004243 A1 | 1/2009 | Pacetti et al. |
| 2009/0035350 A1 | 2/2009 | Stankus et al. |
| 2009/0082853 A1 | 3/2009 | Dutta |
| 2009/0110713 A1 | 4/2009 | Lim et al. |
| 2009/0286761 A1 | 11/2009 | Cheng et al. |
| 2010/0322992 A1 | 12/2010 | Dugan |
| 2011/0223232 A1 | 9/2011 | Hnojewyj et al. |
| 2014/0178452 A1 | 6/2014 | Dugan |
| 2014/0200654 A1 | 7/2014 | Shulze et al. |

FOREIGN PATENT DOCUMENTS

| | | |
|---|---|---|
| EP | 1470830 | 10/2004 |
| EP | 1 518 517 B1 | 3/2005 |
| EP | 1 600 180 | 11/2005 |
| EP | 1604697 | 12/2005 |
| EP | 2 113 230 A2 | 11/2009 |
| EP | 2 417 943 | 2/2012 |
| EP | 2 578 186 B1 | 4/2013 |
| EP | 1 505 930 B1 | 7/2014 |
| WO | WO 94/09010 | 4/1994 |
| WO | WO 97/35575 | 10/1997 |
| WO | WO 00/50007 | 8/2000 |
| WO | WO 01/87368 | 11/2001 |
| WO | WO 01/87372 | 11/2001 |
| WO | WO 01/87376 | 11/2001 |
| WO | WO 02/07601 | 1/2002 |
| WO | WO 02/13883 | 2/2002 |
| WO | WO 02/18477 | 3/2002 |
| WO | WO 02/26139 | 4/2002 |
| WO | WO 02/47731 | 6/2002 |
| WO | WO 03/000308 | 1/2003 |
| WO | WO 03/035131 | 5/2003 |
| WO | WO 03/082368 | 10/2003 |
| WO | WO 03/090818 | 11/2003 |
| WO | WO 03/094990 | 11/2003 |
| WO | WO 2006/014270 | 2/2006 |
| WO | WO 2006/104894 | 10/2006 |
| WO | WO 2007/149825 | 12/2007 |
| WO | WO 2008/016528 | 2/2008 |
| WO | WO 2010/019721 | 2/2010 |

OTHER PUBLICATIONS

Jain, "The manufacturing techniques of carious drug loaded biodegradable poly(lactide-co-glycolide)(PLGA) devices," Biomaterials, 2000, vol. 21, Issue 23, pp. 2475-2490.

European Search Report for 05803287, mailed Apr. 15, 2009, 4 pgs.
International Preliminary Report on Patentability for PCT/US2005/022968, issed Jan. 9, 2007, 8 pages.
Suzuki et al., "Stent-Based Delivery of Sirolimus Reduces Neointimal Formation in a Porcine Coronary Model", Circulation, 104: 1188-1193 (2001).
Tanabe et al., "Local Drug Delivery Using Coated Stents: New Developments and Future Perspectives," *Current Pharmaceutical Design*, 2004, vol. 10, pp. 357-367.
Wieneke et al., "Therapeutic potential of active stent coating", Expert Opinion on Inv. Drugs vol. 12, No. 5, pp. 1354-3784 (2003).
Yokoyama et al., *Characterization of physical entrapment and chemical conjugation of adriamycin in polymeric micelles and their design for in vivo delivery to a solid tumor*, Journal of Controlled Release 50:79-92 (1998).
Büllesfeld et al., "Long-term evaluation of paclitaxel-coated stents for treatment of native coronary lesions", Z. Kardiol 92, pp. 825-832 (2003).
Chao-Wei Hwang et al., "Physiological Transport Forces Govern Drug Distribution for Stent-Based Delivery", Circulation pp. 600-605 (2001).
De Lezo et al., Intracoronary Ultrasound Assessment of Directional Coronary Atherectomy: Immediate and Follow-Up Findings, JACC vol. 21, No. 2, pp. 298-307 (1993).
Grube et al., "Safety and Performance of a Paclitaxel Eluting Stent for the Treatment of In-Stent Restenosis: Preliminary Results of the Taxus III Trial", JACC Angiography & Interventional Cardiology, 1174-15 Abstract, pgs. 58A-59A. (2002).
Grube et al., "Six-and Twelve-Month Results From a Randomized, Double-Blind Trial on a Slow-Release paclitaxel-eluting Stent for De Novo Coronary Lesions", Circulation vol. 7, No. 14, pp. 38-42 (2003).
Lambert et al., "Localized Arterial Wall Drug Delivery From a Polymer-Coated Removable Metallic Stent", Circulation vol. 90, No. 2, pp. 1003-1011 (1994).
Lincoff et al., "Sustained Local Delivery of Dexamethasone by a Novel Intravascular Eluting Stent to Prevent Restenosis in the Porcine Coronary Injury Model", JACC vol. 29, No. 4, pp. 808-816 (1997).
Moreno et al., Macrophage Infiltration Predicts Restenosis After Coronary Intervention in Patients with Unstable Angina, Circulation, vol. 94, No. 12, pp. 3098-3102 (1996).
Neuhaus et al., "mTOR Inhibitors: An Overview", Liver Transplantation, vol. 7, No. 6, pp. 473-484 (2001).
Oikawa et al., Mechanisms of Acute Gain and Late Lumen Loss After Atherectomy in Different Preintervention Arterial Remodeling Patterns, The Am. J. of Cardilogy, vol. 89, pp. 505-510 (2002).
Tanabe et al., "In-Stent Restenosis Treated with Stent-Based Delivery of Paclitaxel Incorporated in a Slow-Release Polymer Formulation", Circulation, pp. 559-564 (2003).
Van der Giessen et al., "Marked Inflammatory Sequelae to Implantation of Biodegradable and Nonbiodegradable Polymers in Porcine Coronary Arteries", Circulation vol. 94, No. 7, pp. 1690-1697 (1996).
Virmani et al., Lessons From Sudden Coronary Death a Comprehensive Morphological Classification Scheme for Atherosclerotic Lesions, Arterioscler Thromb Vasc Biol. pp. 1262-1275.(2000).

* cited by examiner

— 1 —
ANTI-PROLIFERATIVE AND ANTI-INFLAMMATORY AGENT COMBINATION FOR TREATMENT OF VASCULAR DISORDERS WITH AN IMPLANTABLE MEDICAL DEVICE

CROSS-REFERENCE

This application is a division of application Ser. No. 14/192,705, filed on Feb. 27, 2014, published as United States Patent Application Publication No. US 2014-0178452 A1 on Jun. 26, 2014, and issued as U.S. Pat. No. 9,138,337 B2 on Sep. 22, 2015, which is a division of application Ser. No. 12/838,329, filed on Jul. 16, 2010, published as United States Patent Application Publication No. 2010-0322992 A1 on Dec. 23, 2010, and issued as U.S. Pat. No. 8,709,469 on Apr. 29, 2014, which is a continuation-in-part of application Ser. No. 11/090,507, filed on Mar. 24, 2005, and issued as U.S. Pat. No. 7,758,881 on Jul. 20, 2010, which is a continuation-in-part of application Ser. No. 10/882,506, filed on Jun. 30, 2004, and published as United States Patent Application Publication No. 2006-0002968 A1 on Jan. 5, 2006; all four of which are incorporated by reference herein.

BACKGROUND OF THE INVENTION

1. Field of the Invention

This invention generally relates to a drug combination including an anti-proliferative drug such as everolimus and an anti-inflammatory agent such as clobetasol for the treatment of a disorder such as restenosis and vulnerable plaque.

2. Description of the Background

Plaques have been associated with stenosis and restenosis. While treatments of plaque-induced stenosis and restenosis have advanced significantly over the last few decades, the morbidity and mortality associated with vascular plaques have remained significant. Recent work suggests that plaque may generally fall into one of two different general types: standard stenotic plaques and vulnerable plaques. Stenotic plaque, which is sometimes referred to as thrombosis-resistant plaque, can generally be treated effectively by the known intravascular lumen opening techniques. Although plaques induce stenoses, these atherosclerotic plaques themselves are often a benign and are an effectively treatable disease.

Unfortunately, as plaque matures, narrowing of a blood vessel by a proliferation of smooth muscle cells, matrix synthesis, and lipid accumulation may result in formation of a plaque which is quite different than a standard stenotic plaque. Such atherosclerotic plaque becomes thrombosis-prone, and can be highly dangerous. This thrombosis-prone or vulnerable plaque may be a frequent cause of acute coronary syndrome.

While the known procedures for treating plaque have gained wide acceptance and have shown good efficacy for treatment of standard stenotic plaques, they may be ineffective (and possibly dangerous) when thrombotic conditions are superimposed on atherosclerotic plaques. Specifically, mechanical stresses caused by primary treatments like percutaneous transluminal intervention (PTI), such as stenting, may actually trigger release of fluids and/or solids from a vulnerable plaque into the blood stream, thereby potentially causing a coronary thrombotic occlusion. For example, rupture of the fibrous cap that overlies the thrombogenic necrotic core is presently believed to play an important role in acute ischemic events, such as stroke, transient ischemic attack, myocardial infarction, and unstable angina (Virmani R, et al. *Arterioscler Thromb Vasc Biol.* 20: 1262-1275 (2000)). There is evidence that fibrous cap can be ruptured during stent deployment. Human data from various sources have indicated that lipid rich and/or positively remodeled and/or echolucent lesions in symptomatic coronary atherosclerosis have higher likelihood for restenosis (See, for example, *J. Am. Coll. Cardiol.* 21(2):298-307 (1993); *Am. J. Cardiol.* 89(5):505 (2002); *Circ.* 94(12):3098-102 (1996)). Therefore, there is a need for the treatment of vulnerable plaques and restenosis.

Furthermore, it may be desirable for PTI treatments to employ biodegradable implantable medical devices. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers should be configured to completely erode only after the clinical need for them has ended.

However, one of the major clinical challenges of bioabsorbable stents is adequately suppressing acute or chronic inflammatory responses triggered by the degradation of the stent. The vascular response to a fully bioabsorbable stent can be much different than that of a metal or polymer coated stent. Anti-proliferative drugs are often sufficient to reduce neointimal formation, but do not have the ability to adequately suppress inflammation. This is reflected by the large number of granulomas often seen in chronic porcine studies with drug eluting stents.

The embodiments of the present invention address these and other needs.

SUMMARY OF THE INVENTION

Various embodiments of the present invention include a drug-delivery system, comprising: an effective amount of an anti-proliferative agent; a body structure of an implantable medical device comprising at least one depot within the body structure, wherein the at least one depot has an opening on a surface of the body structure and a depth within the body structure; and an effective amount of a steroidal anti-inflammatory agent or a non steroidal anti-inflammatory agent deposited within the depot for the treatment of a vascular disorder or a related disorder; wherein the anti-proliferative agent is everolimus and the steroidal or non-steroidal anti-inflammatory agent is clobetasol, and wherein the ratio of the dose of everolimus to the dose of clobetasol is 1:1 to 3:1 on a molar basis.

Further embodiments of the present invention include a method of treating restenosis or vulnerable plaque of a blood vessel comprising: administering to a patient an effective amount of an anti-proliferative agent; and allowing an effective amount of a steroidal anti-inflammatory agent or a non steroidal anti-inflammatory agent to elute to a vessel from within at least one depot within a body structure of an implantable medical device, wherein the at least one depot has an opening on a surface of the body structure and a depth within the body structure, wherein the combination of the anti-proliferative and anti-inflammatory agents is for treatment of restenosis or vulnerable plaque; wherein the anti-proliferative agent is everolimus and the steroidal or non-steroidal anti-inflammatory agent is clobetasol, and wherein the ratio of the dose of everolimus to the dose of clobetasol is 1:1 to 3:1 on a molar basis.

Additional embodiments of the present invention include a stent, comprising: an effective amount of an anti-proliferative agent; a body structure of an implantable medical device; and an effective amount of a steroidal anti-inflammatory agent or a non steroidal anti-inflammatory agent mixed or dispersed throughout the body structure of the stent for the treatment of a vascular disorder or a related disorder.

Other embodiments of the present invention include a method of treating restenosis or vulnerable plaque of a blood vessel comprising: implanting a stent in a blood vessel, wherein the stent comprises a scaffolding structure made of a bioabsorbable polymer, wherein an effective amount of a steroidal anti-inflammatory agent or a non steroidal anti-inflammatory agent is mixed or dispersed throughout the scaffolding structure; administering to a patient an effective amount of an anti-proliferative agent; and allowing an effective amount of a steroidal anti-inflammatory agent or a non steroidal anti-inflammatory agent to elute to a vessel from a body structure, wherein the combination of the anti-proliferative and anti-inflammatory agents is for treatment of restenosis or vulnerable plaque.

DETAILED DESCRIPTION

Anti-Proliferative Agents and Anti-Inflammatory Agents

Figure 1:
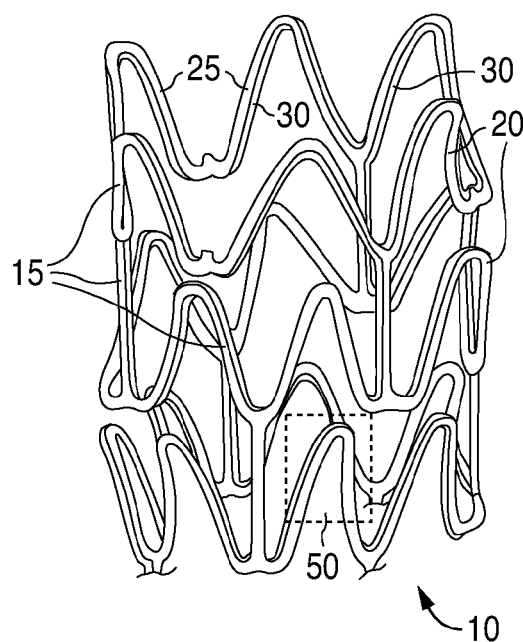
FIG. 1 depicts an illustration of a stent.

In accordance with one embodiment, described herein are a drug-delivery system and the method of using the drug-delivery system. The term "treatment" includes prevention, reduction, delay or elimination of the vascular disorder. In some embodiments, treatment also includes repairing damage caused by the disorder and/or the mechanical intervention. The drug-delivery system has two or more drugs for treating a vascular disorder or a related disorder. The drugs can be a combination of at least one anti-proliferative agent, at least one anti-inflammatory agent, and optionally a third bioactive agent.

In one embodiment, the composition described herein includes an effective amount of at least one anti-inflammatory agent and an effective amount of an anti-proliferative agent. In another embodiment, the composition described herein includes an effective amount of an agent which is effective both as an anti-inflammatory agent and as an anti-proliferative agent.

In some embodiments, the anti-proliferative agent can be everolimus (available under the trade name Certican™, Novartis Pharma AG, Germany), and the anti-inflammatory agent can be clobetasol (available under the trade name Temovate™, Glaxosmithkline, UK).

The anti-proliferative agent and the anti-inflammatory agent can be in the form of a coating with and/or without a polymer matrix on a medical device or at least one of the agents can be administered in a separate dose form such as bolus dose of a free drug, optionally with fluoroscopic dye, or bolus dose of a gel encapsulating a drug. The drug-delivery system or composition may further include a third agent such as a high-density lipoprotein mimetic (HDL-mimetic). For example, an anti-inflammatory agent such as clobetasol can be delivered along with the catheter based delivery of a HDL-mimetic while everolimus is administered by a stent.

The drug-delivery system or composition disclosed herein can be used to treat or prevent a disorder such as thrombosis, high cholesterol, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, restenosis and progression of atherosclerosis in patient subsets including type I diabetics, type II diabetics, metabolic syndrome and syndrome X, vulnerable lesions including those with thin-capped fibroatheromatous lesions, systemic infections including gingivitis, hellobacteria, and cytomegalovirus, and combinations thereof.

Inflammation in Stenting a Vessel

A common disorder in association with mechanical modification of a vessel, such as by a balloon or stenting is restenosis. A number of cellular mechanisms have been proposed that lead to restenosis of a vessel. Two of these mechanisms are (1) the migration and proliferation of smooth muscle cells to and at the site of injury, and (2) the acute and chronic inflammatory response to injury and foreign body presence.

Inflammation is a defensive, biological response to injury, infection or an abrupt change in tissue homeostasis. Inflammation can occur anywhere in the body, and most of the time is confined to that part of the body. Well-known indicators of inflammation are pain, redness, warmth, swelling, and loss of function. In nature, inflammatory responses are designed to destroy, dilute and isolate injurious agents and then lead to recovery and repair of the affected tissue. The intensity of an inflammatory response can vary from one that is self-limiting, which requires minor therapeutic intervention, to one that is life threatening, which requires intense intervention. One drawback of the inflammatory process is its ability to become progressive, meaning tissue damage continues after the stimulus is neutralized or removed.

Vascular inflammation is the first stage of the inflammatory response, developing after the initial contact with the stimulus and continuing sometimes for several days. The presence of a stimulatory agent in the blood or in the tissue triggers the body's response through endothelial cells. The endothelial cell layer is the innermost layer of larger vessels and the only cell layer of the smallest vessels, the capillaries. Endothelial cells produce substances called chemokines that attract neutrophils and other white blood cells to the site of injury. Within the site, neutrophils and endothelium relay information back and forth across cell membranes through presentation of adhesion molecules and cytokines Cellular cross-talk promotes physical interaction between the "inflamed" neutrophil and the "inflamed" endothelium.

Additionally, the presence of a biodegradable foreign body, such as a biodegradable implantable medical device (e.g., a stent), in a vessel can lead to or aggravate an inflammatory response, thus leading to a more aggressive restenotic process. Biodegradation refers generally to changes in physical and chemical properties that occur (e.g., in a polymer) upon exposure to bodily fluids as in a vascular environment. The changes in properties may include a decrease in molecular weight, deterioration of mechanical properties, and decrease in mass due to erosion or absorption. The decrease in molecular weight may be caused by chemical reactions of bodily fluids with the polymer, for example, hydrolysis and/or metabolic processes. By-products of such degradation reactions can be responsible for inciting inflammation. For example, by-products of hydrolysis are produced when polymer molecules are cleaved into component parts by the addition of water. Various byproducts of degradation of biodegradable polymers are known to incite an inflammatory response. For example, lactic acid, a degradation by-product of poly(lactic acid) polymers, is known to cause an inflammatory response.

Furthermore, the release of by-products into the body from a biodegradable device occurs continuously from the time of first exposure to bodily fluids to a time when the device is either completely degraded and eliminated or removed from the body. It follows that throughout this time frame, the body is continuously exposed to inflammation-inciting by-products. Therefore, it is desirable to have a sustained release of an anti-inflammatory agent from a degrading implanted device throughout this time frame.

Another important pathological feature of vascular inflammation is endothelial cell swelling. This action reduces the functional vessel diameter such that the speed of blood flow falls significantly and the vessel becomes congested. When these conditions predominate, inflamed neutrophils are induced to plug the vessel. As a result, endothelial cells lose their tight connections allowing neutrophils to transmigrate into the surrounding tissue.

Within hours of the initial stimulus, neutrophils begin to enter the tissue and may continue transmigration for many days. The appearance of inflammatory cells in the surrounding tissue marks the beginning of tissue damage. In some inflammatory conditions, tissue damage is caused by direct injury of the vessels and amplified by the subsequent recruitment of neutrophils into the tissue.

Activated by local mediators, neutrophils and tissue macrophages are triggered to release agents that destroy toxins and clean up dead cells in the area. Unfortunately, these same agents also cause collateral damage to healthy cells, which further extends the borders of the initial tissue destruction.

Tissue repair is the third and final stage of inflammation. It may take several days for tissue destruction to reach full intensity before tapering off. Until then, the tissue repair process that consists of growth of new blood vessels and entry of monocytes to clean up the debris is delayed. Fibroblasts also enter the local tissue to replace the extracellular matrix and collagen. The process of tissue repair is stringently controlled within the tissue site. If the process becomes dysregulated, inappropriate tissue repair will lead to excessive scarring. Depending on the tissue and the intensity/duration of the inflammatory condition, the amount of scarring can be significant.

An example of disorders that vessel inflammation is involved is vulnerable plaque (VP) rupture. Previous studies have demonstrated that inflammation promotes proliferation at sites of balloon angioplasty and stent placement in pigs (Kornowski, et al., Coron Artery Dis. 12(6):513-5 (2001)). Since sites of vulnerable plaque have a higher density of macrophages and lymphocytes than other types of atherosclerotic lesions, it is expected that these sites, when stented, will produce elevated amounts of the cytokines (IL-1, TNF-alpha) that promote smooth muscle cell proliferation.

Another example of disorders that vessel inflammation is involved is diabetes. Studies have shown that patients with type-2 diabetes have higher rates of restenosis than the general population. The diabetic patient is in pro-inflammatory state that can amplify restenosis because diabetic lesions contain a large number of inflammatory cells (e.g., macrophages, lymphocytes, etc.).

Implantable Medical Devices

The term "implantable medical device" is intended to include self-expandable stents, balloon-expandable stents, stent-grafts, and grafts. An implantable medical device includes a body structure, substrate, or scaffolding. The structure of the device can be of virtually any design. A stent, for example, may include a pattern or network of interconnecting structural elements or struts. FIG. 1 depicts an example of a three-dimensional view of a stent 10. The stent may have a pattern that includes a number of interconnecting elements or struts 15. The embodiments disclosed herein are not limited to stents or to the stent pattern illustrated in FIG. 1. For example, the cross-section of a strut may be rectangular, (as pictured in FIG. 1), circular, oval, etc.

The struts of the stent in FIG. 1 may further be described as having abluminal (outer) faces 20, luminal (inner) faces 25, and sidewalls 30. The embodiments are easily applicable to other patterns and other devices. In general, the variations in the structure of patterns are virtually unlimited. As shown in FIG. 1 the geometry or shape of stents vary throughout its structure.

In some embodiments, a stent may be formed from a tube by laser cutting the pattern of struts into the tube. The stent may also be formed by laser cutting a polymeric or metallic sheet, rolling the pattern into the shape of the cylindrical stent, and providing a longitudinal weld to form the stent. Other methods of forming stents are well known and include chemically etching a sheet and rolling and then welding it to form the stent. A polymeric or metallic wire may also be coiled to form the stent. The stent may be formed by injection molding of a thermoplastic or reaction injection molding of a thermoset polymeric material. Filaments of the compounded polymer may be extruded or melt spun. These filaments can then be cut, formed into ring elements, welded closed, corrugated to form crowns, and then the crowns welded together by heat or solvent to form the stent. Lastly, hoops or rings may be cut from tubing stock, the tube elements stamped to form crowns, and the crowns connected by welding or laser fusion to form the stent.

The underlying structure or substrate of an implantable medical device, such as a stent can be completely or at least in part be made from a biodegradable polymer or combination of biodegradable polymers, a biostable polymer or combination of biostable polymers, or a combination of biodegradable and biostable polymers. Additionally, a polymer-based coating for a surface of a device can be a biodegradable polymer or combination of biodegradable polymers, a biostable polymer or combination of biostable polymers, or a combination of biodegradable and biostable polymers.

Anti-Proliferative Agents

Any drugs having anti-proliferative effects can be used in the present invention. The anti-proliferative agent can be a natural proteineous agent such as a cytotoxin or a synthetic molecule. Preferably, the active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck) (synonyms of actinomycin D include dactinomycin, actinomycin IV, actinomycin $I_1$, actinomycin $X_1$, and actinomycin $C_1$), all taxoids such as taxols, docetaxel, and paclitaxel, paclitaxel derivatives, all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Representative rapamycin derivatives include 40-O-(3-hydroxy)propyl-rapamycin, 40-O-[2-(2-hydroxy)ethoxy]ethyl-rapamycin, or 40-O-tetrazole-rapamycin, 40-epi-(N1-tetrazolyl)-rapamycin (ABT-578 manufactured by Abbot Laboratories, Abbot Park, Ill.), prodrugs thereof, co-drugs thereof, and combinations thereof.

In one embodiment, the anti-proliferative agent is everolimus. Everolimus acts by first binding to FKBP12 to form a complex (Neuhhaus, P., et al., Liver Transpl. 2001 7(6):473-84 (2001) (Review)). The everolimus/FKBP12 complex then binds to mTOR and blocks its activity (Id.). By blocking mTOR activity, cells are unable to pass through G1 of the cell cycle and as a result, proliferation is inhibited. mTOR inhibition has also been shown to inhibit vascular smooth muscle migration.

Anti-inflammatory Agents

Any drugs having anti-inflammatory effects can be used in the present invention. The anti-inflammatory drug can be a steroidal anti-inflammatory agent, a nonsteroidal anti-inflammatory agent, or a combination thereof. In some embodiments, anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof.

In one embodiment, the anti-inflammatory agent is clobetasol. Clobetasol is a corticosteroid that binds to corticosteroid receptors, a class of nuclear receptor. The binding of clobetasol to the corticosteroid receptor subsequently alters gene expression in such a way that inflammation is inhibited. For example, corticosteroids inhibit the activation of NFkB, the nuclear factor that is responsible for changes in gene expression that promote inflammation. The reduction in inflammation may also inhibit the mechanisms that promote small muscle cell (SMC) hyper proliferation. This is shown in that dexamethasone, a less potent glucocorticoid as compared to clobetasol, reduces the production of PGDF and thus has anti-proliferative properties. Clobetasol acts through similar pathways and is more potent than dexamethasone.

Dosage

The dosage or concentration of the anti-proliferative and anti-inflammatory agents required to produce a favorable therapeutic effect should be less than the level at which the bioactive agent produces toxic effects and greater than the level at which non-therapeutic results are obtained. The dosage or concentration of the agents required can depend upon factors such as the particular circumstances of the patient, the nature of the trauma, the nature of the therapy desired, the time over which the ingredient administered resides at the vascular site, and if other active agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies.

In one embodiment, the bioactive agents can be incorporated into polymeric coating in a percent loading of between about 0.01% and less than about 100% by weight, more preferably between about 5% and about 50% by weight of the total drug-load that includes greater than about 0% to about 100% of the anti-proliferative agent and less than about 100% to greater than about 0% of the anti-inflammatory agent. The relative amount of the anti-proliferative agent and anti-inflammatory agent can be determined by the type of lesions to be treated. For example, where everolimus is used as the anti-proliferative agent and clobetasol is used as the anti-inflammatory agent, the relative amount of everolimus and clobetasol can be varied for different types of lesions, that is, the relative amount of everolimus can be higher for more proliferative lesions, and on the other hand, the relative amount of clobetasol can be higher for more inflammatory lesions.

Other Bioactive Agents

In some embodiments, other agents can be used in combination with the anti-proliferative agent and the anti-inflammatory agents. These bioactive agents can be any agent which is a therapeutic, prophylactic, or diagnostic agent. These agents can also have anti-proliferative and/or anti-inflammatory properties or can have other properties such as antineoplastic, antiplatelet, anti-coagulant, anti-fibrin, anti-thrombotic, antimitotic, antibiotic, antiallergic, antioxidant as well as cystostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax™ (bivalirudin, Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium.

Other therapeutic substances or agents which may be appropriate include alpha-interferon, and genetically engineered epithelial cells. The foregoing substances are listed by way of example and are not meant to be limiting. Other active agents which are currently available or that may be developed in the future are equally applicable.

Delivery Formulations

The composition comprising both anti-proliferative agent and the anti-inflammatory agent can be formulated into any formulation suitable for delivery by any mode of delivery. For example, the composition can be formed into a coating on an implantable medical device to provide controlled release of the anti-proliferative agent and the anti-inflammatory agent. The composition can also be formulated into other suitable formulations for example, bolus dose of free drug, optionally with a fluoroscopic dye, bolus dose of gel-encapsulated drug.

The gel can be formed of a gel-forming material or polymer such as hyaluronic acid, carboxymethyl cellulose, pectin, hydroxypropyl methylcellulose, hydroxypropyl cellulose, methylcellulose, sodium carboxymethylcellulose, hydroxyethylcellulose, polyethylene oxide, acacia, tragacanth, guar gum, xanthan gum, locust bean gum, Carbopol™ acidic carboxy polymer, polycarbophil, polyethylene oxide, poly(hydroxyalkyl methacrylate), poly (electrolyte complexes), poly(vinyl acetate) cross-linked with hydrolyzable bonds, water-swellable N-vinyl lactams polysaccharides, natural gum, agar, agarose, sodium alginate, carrageenan, fucoidan, furcellaran, laminaran, hypnea, eucheuma, gum arabic, gum ghatti, gum karaya, arbinoglactan, amylopectin, gelatin, hydrophilic colloids such as carboxylmethyl cellulose gum or alginate gum, including both non-crosslinked and crosslinked alginate gums, where the crosslinked alginate gums may be crosslinked with di- or trivalent ions, polyols such as propylene glycol, or other crosslinking agents, Cyanamer™ polyacrylamides, Goodrite™ polyacrylic acid, starch graft copolymers, Aqua-Keeps™ acrylate polymer, ester crosslinked polyglucan, and the like, and combinations thereof. Some of the gel-forming materials are discussed in U.S. patents, U.S. Pat. Nos. 3,640,741, 3,865,108, 3,992,562, 4,002,173, 4,014,335, and 4,207,893. Hydrogels also are discussed in the Handbook of Common Polymers, by Scott and Roff, published by the Chemical Rubber Company, Cleveland, Ohio. For any given gel-forming material or polymer, use of a material with higher average molecular weight provides higher viscosity in aqueous solution of any given concentration. Therefore, using a higher molecular weight generally enables use of a lesser quantity of polymer to accomplish the required retardation of dissolution. In some embodiments, the gel-forming material or polymer can be hydroxypropyl methylcellulose having 19-24% methoxyl substitution and 7-12% hydroxypropyl substitution and a number average molecular weight of at least 20,000. Such polymers include those sold by Dow Chemical Co. under the tradenames Methocel®, Methocel K4M, Methocel K15M and Methocel K100M.

Modes of Delivery

In one embodiment, the anti-inflammatory drug such as clobetasol is formulated into a bolus dose of free drug with, optionally, a fluoroscopic dye. The anti-proliferative drug such as everolimus can be formulated into a coating composition with a polymeric material and then coated onto an implantable device (e.g., stent). The bolus dose of anti-inflammatory drug is administered first and then the anti-proliferative drug is delivered by release from the implantable device such as a drug-delivery stent. The composition may further include a third agent such as a HDL (high density lipoprotein)-mimic as described in U.S. Pat. No. 6,367,479. Alternatively, HDL-mimic can be delivered by the stent.

In another embodiment, the anti-inflammatory drug such as clobetasol is formulated into a bolus dose of gel. The anti-proliferative drug such as everolimus can be formulated into a coating composition with a polymeric material and then coated onto an implantable device. The bolus dose of the anti-inflammatory drug is administered first and then the anti-proliferative drug is delivered by release from the implantable device such as a drug-delivery stent.

In a further embodiment, the anti-inflammatory drug and the anti-proliferative drug can be included in a polymeric matrix and then coated onto a medical device such as a stent. The medical device coating can be designed to have a variety of different release parameters for each of the drugs included in the coating.

As indicated above, the release of inflammation-inciting by-products into the body from a biodegradable device can occur continuously while the device is degrading within the body. Therefore, embodiments of a drug-delivery system having a sustained release of an anti-inflammatory agent from an implanted device are described.

Certain embodiments of a drug-delivery system may include an effective amount of an anti-proliferative agent. The drug delivery system may further include a body structure of an implantable medical device. In some embodiments, the body structure may be a substrate or scaffolding of an implantable medical device, such as stent. The substrate or scaffolding may be a biostable or bioabsorbable polymer. An embodiment of the drug-delivery system may further include an effective amount of a steroidal anti-inflammatory agent or a non steroidal anti-inflammatory agent within the body structure of the device. In some embodiments, an amount of therapeutic agent such as a steroidal anti-inflammatory agent or a non steroidal anti-inflammatory agent can be mixed or dispersed throughout an entire volume of the body structure of the device or throughout an entire volume of portions of structural elements of the body structure. In exemplary embodiment, the body structure includes a scaffolding including a plurality of structural elements or struts, as shown in FIG. 1. The agent can be mixed or dispersed within and/or throughout the entire volume of a length of a strut or entire volume of all the struts. In some embodiments, agent can be uniformly or relatively uniformly mixed or dispersed through the volume of a length of a strut or all of the struts. In such embodiments, the dispersion of the agent is not limited to only a region of volume, for example, only near a surface region of a strut. The body structure, such as the plurality of struts, may further have a coating on or above at least a portion of its surface that includes or is composed of the same or different polymer as the body structure. The coating may be free of the agent in the body structure, except for incidental diffusion prior to implantation. After implantation the agent in the body structure may diffuse into and through the coating. The coating may be a polymer and may further include a different agent than the body structure, such as an anti-proliferative agent.

In some embodiments, the agent is dispersed throughout an entire volume of a body structure within biodegradable material, such as a biodegradable polymer. An anti-inflammatory agent within a biodegradable body structure may allow for sustained release of the inflammatory agent throughout the degradation process of the body structure. For example, the agent may be released from the body structure into a host in which a device is implanted as the body structure degrades and erodes (loses mass). The agent may be released partially or completely through degradation or erosion of the body structure in which it is dispersed. The agent may also be released partially or completely through diffusion from the body structure.

In one embodiment, at least some of the anti-proliferative agent may be contained in a coating on the body structure of the device. The coating may be pure or substantially pure agent or mixed or dispersed in a biostable or bioabsorbable polymer matrix. Alternatively, at least some of the anti-proliferative agent may be delivered in some other local manner or systemically.

An embodiment of a method of treating restenosis or vulnerable plaque of a blood vessel may include administering to a patient an effective amount of an anti-proliferative agent either through a coating on a device, systemically, and/or some other local method. The method may further include allowing an effective amount of a steroidal anti-inflammatory agent or a non steroidal anti-inflammatory agent to elute to a vessel from within a body structure the device. At least a portion of the anti-inflammatory agent in at least one depot and/or anti-inflammatory agent mixed or dispersed within the body structure may elute from a surface of the body structure. In some embodiments, the anti-inflammatory agent may elute through a coating containing at least a portion of the anti-proliferative agent. At least a portion of the anti-inflammatory agent may elute from the body structure and suppress inflammation of a blood vessel during all or a majority of the degradation of the body structure.

Moreover, the properties of the coating, such as thickness and porosity, may influence the rate of release of the anti-inflammatory agent from the device. Some embodiments may include controlling the release rate of anti-proliferative agent by modifying the properties of the coating.

In one embodiment, at least a portion of the anti-inflammatory agent within the body structure may be contained in at least one depot or cavity on at least a portion of a surface of the body structure. The agent in the depot may be pure or substantially pure agent. Alternatively, the agent in the depot may be mixed or dispersed in a polymer matrix.

Numerous embodiments of implantable medical devices with depots configured to hold an agent are possible. Depots may be placed at one or more arbitrary locations on a device. In some embodiments, depots may be selectively distributed at or near portions of a device that are adjacent to regions of a vessel in need of treatment for inflammation. For example, in long lesions, the center portion of the lesion may be more inflamed than the ends of the lesion. The greater inflammation may arise from a larger concentration of degradation products closer to the center of the stent than the ends of the stent. Thus, the center of the lesion may require more anti-inflammatory agent than the ends of the lesion. Alternatively, the ends of the lesion may be more inflamed due to mechanical stresses causing irritation or injury to the ends of the lesion. Thus, a stent may include depots or more depots in regions of a stent adjacent portions of a lesion having more inflammation.

Figure 2:
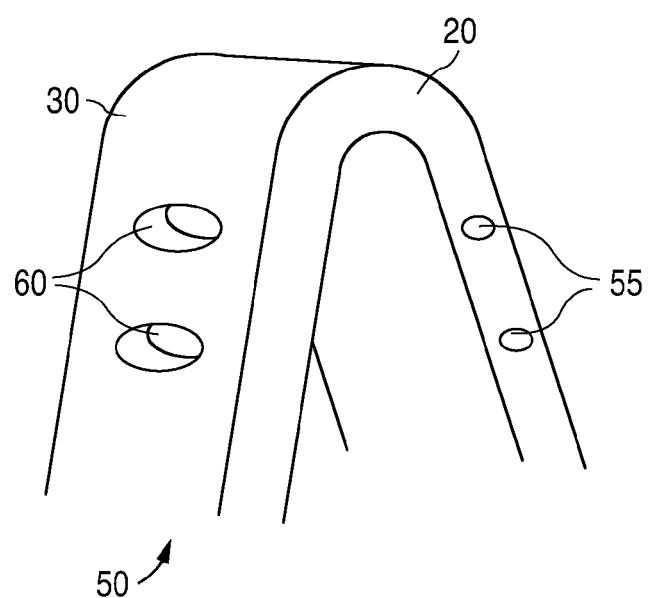
FIG. 2 depicts an illustration of a section of a stent.

Additionally, depots may be selectively disposed on abluminal faces, luminal faces, and/or sidewalls of a stent. For example it may be desirable to have depots on abluminal faces since they may be in contact with inflamed portions of a vessel. However, depots may be placed at any location on a stent that could be clinically beneficial in treating restenosis. FIG. 2 depicts a section 50 of stent 10 from FIG. 1. In section 50, depots 55 are disposed on an abluminal face 20 and depots 60 are disposed on a sidewall 30.

Additionally, the geometrical parameters that characterize depots such as size (e.g., depth, diameter, etc.) and shape may be configured to facilitate treatment of an inflammatory response. For example, the geometry of depots may be configured to maximize sustained delivery of anti-inflammatory agent throughout the degradation of a device to counteract the inflammatory effect of degradation by-products.

A single depot or plurality of depots may be formed as a laser trench or laser trenches on a body of an implantable medical device such as stent 10 by exposing a surface of the device to an energy discharge from a laser, such as an excimer laser. Alternative methods of forming depots include, but are not limited to physical or chemical etching techniques. Techniques of laser fabrication or etching to form depots are well-known to one of ordinary skill in the art. Depots can be formed in virtually any stent structure and not merely the above-described structure.

Figure 3A:
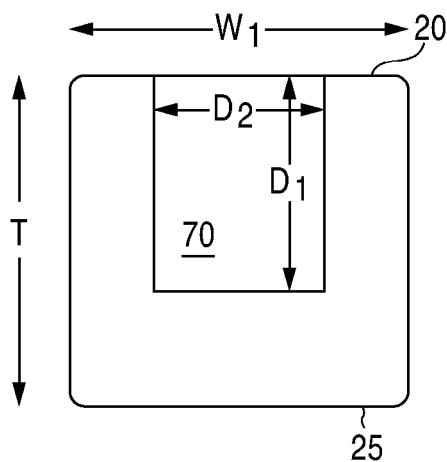
FIGS. 3A-B depict cross-sections of a strut illustrating geometries of depots.
Figure 3B:
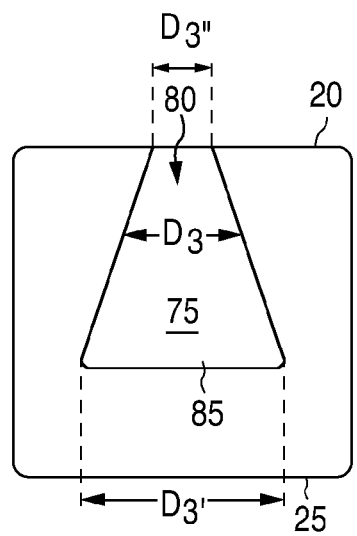

FIGS. 3A-B depict cross-sections of a strut illustrating geometries of depots. Referring to FIG. 3A, depot 70 has a generally cylindrical shape. Depot 70 has a depth $D_1$ and diameter $D_2$. The appropriate values for $D_1$ and $D_2$ depend on factors such as the effective amount of agent, mechanical integrity of the strut, density of depots, and the desired time frame of release of active agent. For instance, the greater the effective amount of agent, the larger either or both depth $D_1$ and diameter $D_2$ may need to be. A higher density of depots disposed on a strut may decrease a required amount of agent in an individual strut, and thus a necessary size of a depot. Furthermore, as the size and density of the depots increase, the mechanical strength of the strut may decrease. Additionally, a longer sustained release of active agent may be facilitated by a larger depth $D_1$. A diameter $D_2$ of cylindrical depot 70 may have a range from about 10% to about 95%, about 20% to about 80%, 30% to about 70%, or about 40% to about 60% of width $W_1$.

FIG. 3B illustrates a depot 75 which is generally conical in shape. Conical shaped depot 75 has an open end 80 and a closed end 85. Open end 80 is the end that contacts a surface of a tissue since open end 80 is at abluminal face 20. A diameter $D_3$ of conical shaped depot 75 is shown to decrease from closed end 85 to open end 80. The largest diameter $D_3'$ is at the closed end 85 of conical shaped depot 75. $D_3'$ may have a range from about 10% to about 95%, about 20% to about 80%, 30% to about 70%, or about 40% to about 60% of width $W_1$. The smallest diameter $D_3''$ at open end 80 of conical shaped depot 75 may have a range from about 1% to about 70%, about 5% to about 70%, about 15% to about 60% of about 30% to about 50% of width $W_1$. The reduced size of opening 80 of conical shaped depot 75, as compared to that of the cylindrical shaped depot 70, may reduce the rate at which the anti-inflammatory agent is released once the stent is implanted at the desired location of treatment. The depots can have a variety of other geometrical shapes, such as elongated trenches (not illustrated).

In other embodiments, at least a portion of the anti-inflammatory agent within the body structure may be mixed or dispersed within the body structure of the device. The anti-inflammatory agent mixed or dispersed within a biodegradable body structure may elute into a vessel at substantially the same rate as the body structure degrades. In one embodiment, the anti-inflammatory agent may be incorporated (mixed or dispersed) within the body structure during fabrication of the device. For example, the agent may be mixed with polymer in a molten state before, during, and/or after a fabrication process such as extrusion or injection molding. However, it is important to control the temperature of a molten polymer containing agent during a mixing process to inhibit or prevent degradation of the active agent. The temperature of a molten polymer may be controlled to be below a degradation temperature or degradation temperature range. Some agents tend to degrade at temperatures above about 80° C. Others may tend to degrade above about 100° C.

Figure 4A:
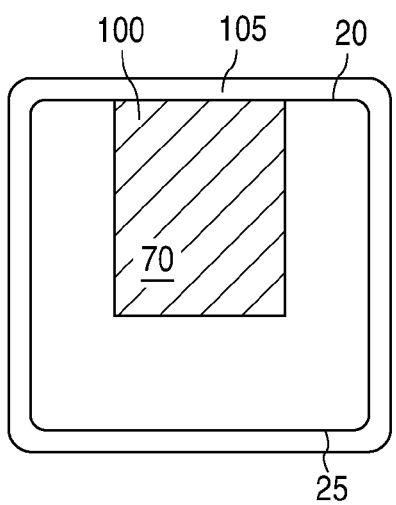
FIGS. 4A-B depicts cross-sections of a strut with a coating.
Figure 4B:
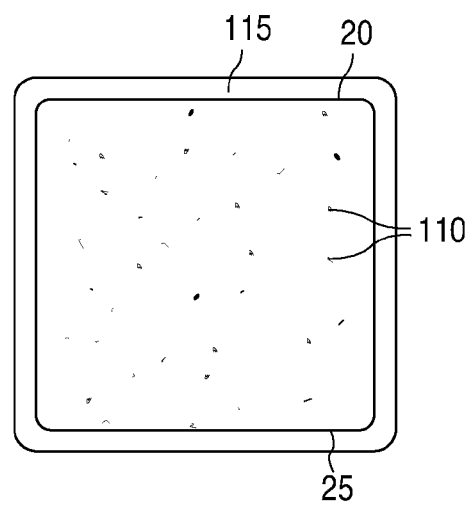

FIGS. 4A-B depict cross-sections of struts having anti-inflammatory agent within that is below a coating 105 and 115. Coating 105 and 115 may include an anti-proliferative agent. As shown in FIGS. 4A-B, coating 105 and 115 completely surrounds or covers the surface of the strut, covering the abluminal, luminal, and sidewall surfaces of the strut. In FIG. 4A, a composition 100 that is pure anti-inflammatory agent or anti-inflammatory agent dispersed within a polymer matrix is deposited within depot 70. Anti-inflammatory agent is configured to elute through coating 105 to treat inflamed portions of vessels. FIG. 4B depicts an anti-inflammatory agent 110 dispersed within the strut. Anti-inflammatory agent 110 is configured to elute through coating 115 to treat inflamed portions of vessels.

An anti-inflammatory can have one or a combination of release profiles that include a pulse release, fast or burst release, and a sustained release. Similarly, the anti-proliferative drug can have one or a combination of release profiles that include a pulse release, fast or burst release, and a sustained release from the stent. In some embodiments, the combination can be delivered simultaneously or at least during the drug treatment period there is at least some overlap between the release of the drugs. In some embodiments, the anti-inflammatory can be completely released prior to the release to the anti-proliferative or can be partially released with some or significant overlap between the release of both drugs. "Pulse release" generally refers to a release profile of a drug that features a sudden surge of the release rate of the drug. The release rate surge of the drug would then disappear within a period. A more detailed definition of the term can be found in Encyclopedia of Controlled Drug Delivery, Edith Mathiowitz, Ed., Culinary and Hospitality Industry Publications Services.

As used herein, the term "fast release" in one embodiment refers to a release profile of a drug that features a release rate in the range between about 15 to about 40 µg per day for a 18 mm stent, about 10 µg to about 27 µg per day for a 13 mm stent, and about 6.7 µg to about 17.2 µg per day for a 8 mm stent. Equivalent profiles can be derived by one having ordinary skill in the art for stents having other sizes. In another embodiment, the term "fast release" refers to an approximately 20% release in 24 hours of a drug. The term "fast release" is used interchangeably with the term "burst release."

As used herein, the term "sustained release" generally refers to a release profile of a drug that can include zero-order release, exponential decay, step-function release or other release profiles that carry over a period of time, for example, ranging from several days to several years. The terms "zero-order release", "exponential decay" and "step-function release" as well as other sustained release profiles are well known in the art (see, for example, Encyclopedia of Controlled Drug Delivery, Edith Mathiowitz, Ed., Culinary and Hospitality Industry Publications Services).

In one embodiment, at least one of the anti-inflammatory agent (e.g., clobetasol) and anti-proliferative agent (e.g., everolimus) is administered via a stent while the other is administered by other local means of administration or alternatively, the other is administered systemically. In other embodiments, both are administered locally, by means other than a stent, or alternatively systemically. Systemic administration can be accomplished orally or parenterally including intravascularly, rectally, intranasally, intrabronchially, or transdermally. Liquid carriers which are sterile solutions or suspensions can be injected intramuscularly, intraperitoneally, subcutaneously, and intravenously. Rectal administration can be in the form of conventional suppository. For administration by intranasal or intrabronchial inhalation or insufflation, the drug can be formulated into an aqueous or partially aqueous solution, which can then be utilized in the form of an aerosol. The drug can be administered transdermally through the use of a transdermal patch and a carrier that is inert to and mutually compatible with the active component, is non-toxic to the skin, and allows for the delivery of the drug for systemic absorption into the blood stream via the skin. The carrier may take any number of forms such as creams, ointments, pastes, and gels. The creams and ointments may be viscous liquids or semisolid emulsions of either the oil-in-water or water-in-oil type. Pastes made of absorptive powders dispersed in petroleum or hydrophilic petroleum containing the active component may also be suitable. Other devices capable of releasing the drug into the blood stream include semi-permeable membranes covering a reservoir containing the drug, with or without a carrier.

Local administration can be accomplished by a variety of techniques which administer the active component at or near the target site. The following examples of local delivery techniques are provided for illustrative purposes and are not intended to be limiting. Examples include local delivery catheters, site specific carriers, implants, direct application, or direct injection. Local delivery by a catheter allows for the administration of the drug directly to the target site.

Local delivery by site specific carriers is conducted by attaching the drug to a carrier which will direct or link the drug to the target cells. Examples of this delivery technique include the use of carrier such as a protein ligand, a monoclonal antibody or a membrane anchored linker.

Local delivery by an implant (other than a stent) is the placement of a matrix carrying the drug at the site. The matrix can release the active component by, for example, diffusion, degradation, chemical reaction, solvent activators, etc. One example of local delivery by an implant can include direct injection of vesicles or micro-particles. These micro-particles may be composed of substances such as proteins, lipids, carbohydrates or synthetic polymers. The micro-particles can have the drug impregnated therein and/or coated thereon. Application via implants is not limited to the above described routes and other techniques such as grafts, micropumps or application of a fibrin glue or hydrogel containing the active component around the exterior of a designated region of the vessel can also be implemented by one of ordinary skill in the art.

Local delivery by direct injection describes injecting a liquid carrier containing the drug directly into the site. The liquid carrier should be inert to and mutually compatible with the drug. The component can be in true solution or suspended in fine particles in the carrier. A suitable example of an inert carrier includes a sterile saline solution.

Biocompatible and Bioabsorbable Polymers

In general, polymers can be biostable, bioabsorbable, biodegradable, or bioerodable. Biostable refers to polymers that are not biodegradable. The terms biodegradable, bioabsorbable, and bioerodable, as well as degraded, eroded, and absorbed, are used interchangeably and refer to polymers that are capable of being completely eroded or absorbed when exposed to bodily fluids such as blood and can be gradually resorbed, absorbed and/or eliminated by the body.

Representative examples of polymers that may be used to fabricate an implantable medical device, to coat an implantable medical device, or to provide a drug delivery particle with the anti-proliferative drug and/or anti-inflammatory drug include, but are not limited to, poly(N-acetylglucosamine) (Chitin), Chitosan, poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyorthoester, polyanhydride, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in fabricating embodiments of implantable medical devices disclosed herein include ethylene vinyl alcohol copolymer (commonly known by the generic name EVOH or by the trade name EVAL®), poly(butyl methacrylate), poly(vinylidene fluoride-co-hexafluoropropene) (e.g., SOLEF® 21508, available from Solvay Solexis PVDF, Thorofare, N.J.), polyvinylidene fluoride (otherwise known as KYNAR®, available from Atofina Chemicals, Philadelphia, Pa.), ethylene-vinyl acetate copolymers, poly(vinyl acetate), styrene-isobutylene-styrene triblock copolymers, and polyethylene glycol.

Method of Coating a Device

The coating described herein can be formed by spray coating or any other coating process available in the art. Generally, the coating involves dissolving or suspending the composition, or one or more components thereof, in a solvent or solvent mixture to form a solution, suspension, or dispersion of the composition or one or more components thereof, applying the solution or suspension to an implantable device, and removing the solvent or solvent mixture to form a coating or a layer of coating. Suspensions or dispersions of the composition described herein can be in the form of latex or emulsion of microparticles having a size between 1 nanometer and 100 microns, preferably between 1 nanometer and 10 microns. Heat and/or pressure treatment can be applied to any of the steps involved herein. In addition, if desirable, the coating described here can be subjected to further heat and/or pressure treatment. Some additional exemplary processes of coating an implantable device that may be used are described in, for example, Lambert T L, et al. Circulation, 1994, 90: 1003-1011; Hwang C W, et al. Circulation, 2001; 104: 600-605; Van der Giessen W J, et al. Circulation, 1996; 94: 1690-1697; Lincoff A M, et al. J Am Coll Cardiol 1997; 29: 808-816; Grube E. et al, J American College Cardiology Meeting, Mar. 6, 2002, ACCIS2002, poster 1174-15; Grube E, et al, Circulation, 2003, 107: 1, 38-42; Bullesfeld L, et al. Z Kardiol, 2003, 92: 10, 825-832; and Tanabe K, et al. Circulation 2003, 107: 4, 559-64.

As used herein, the term "solvent" refers to a liquid substance or composition that is compatible with the polymer and is capable of dissolving or suspending the polymeric composition or one or more components thereof at a desired concentration. Representative examples of solvents include chloroform, acetone, water (buffered saline), dimethylsulfoxide (DMSO), propylene glycol monomethyl ether (PM), iso-propylalcohol (IPA), n-propyl alcohol, methanol, ethanol, tetrahydrofuran (THF), dimethylformamide (DMF), dimethyl acetamide (DMAC), benzene, toluene, xylene, hexane, cyclohexane, heptane, octane, nonane, decane, decalin, ethyl acetate, butyl acetate, isobutyl acetate, isopropyl acetate, butanol, diacetone alcohol, benzyl alcohol, 2-butanone, cyclohexanone, dioxane, methylene chloride, carbon tetrachloride, tetrachloroethylene, tetrachloro ethane, chlorobenzene, 1,1,1-trichloroethane, 1,1,2-trichloroethane, formamide, hexafluoroisopropanol, 1,1,1-trifluoroethanol, and hexamethyl phosphoramide and a combination thereof.

Examples of such implantable devices include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE® and ENDOTAK,® available from Guidant Corporation, Santa Clara, Calif.). The underlying structure of the device can be of virtually any design. The device can be made of a metallic material or an alloy such as, but not limited to, cobalt chromium alloy (ELGILOY®), stainless steel (316L), high nitrogen stainless steel, e.g., BIODUR 108, cobalt chrome alloy L-605, "MP35N," "MP20N," ELASTINITE® (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention. In one embodiment, the implantable device is a stent, which can be degradable stents, biodurable stents, depot stents, and metallic stents such as stents made of stainless steel or nitinol. The stents can be balloon expandable or self-expanding.

Method of Use

In accordance with embodiments of the invention, a coating of the various described embodiments can be formed on an implantable device or prosthesis, e.g., a stent. For coatings including one or more active agents, the agent will be retained on the medical device such as a stent during delivery and expansion of the device, and released at a desired rate and for a predetermined duration of time at the site of implantation. Preferably, the medical device is a stent. A stent having the above-described coating is useful for a variety of medical procedures, including, by way of example, treatment of obstructions caused by tumors in bile ducts, esophagus, trachea/bronchi and other biological passageways. A stent having the above-described coating is particularly useful for treating occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

The implantable device comprising a coating described herein can be used to treat an animal having a condition or disorder that requires a treatment. Such an animal can be treated by, for example, implanting a device described herein in the animal. Preferably, the animal is a human being. Exemplary disorders or conditions that can be treated by the method disclosed herein include, but not limited to, thrombosis, high cholesterol, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, restenosis and progression of atherosclerosis in patient subsets including type I diabetics, type II diabetics, metabolic syndrome and syndrome X, vulnerable lesions including those with thin-capped fibroatheromatous lesions, systemic infections including gingivitis, hellobacteria, and cytomegalovirus, and combinations thereof.

EXAMPLES

The embodiments of the present invention will be illustrated by the following set forth examples. All parameters and data are not to be construed to unduly limit the scope of the embodiments of the invention.

Example 1

Porcine Implant Study

Described in this example is a 28 day porcine implant study that compared the 200 μg/cm$^2$ dose Lemans with a clobetasol-only delivery stent, an everolimus-only stent, and an everolimus-clobetasol combination drug delivery stent. The study was performed using three different drug delivery stents, Arm 1, Arm 2, and Arm 3. Arm 1 is a Lemans stent (a stent available from Guidant based on PVDF-co-HFP) that included 105 μg everolimus and used as a control. Arm 2 was loaded with 185 μg clobetasol only, with no everolimus. Arm 3 is loaded with 105 μg everolimus and 80 μg clobetasol.

The Arm 1, Arm 2, and Arm 3 stents were implanted in a 30% overstretch model. Overstretch model refers to the technique of overexpanding the animal arteries by up to 30% (using the stent and balloon) over their natural diameter so that the stent is more likely to cause injury and thus greater restenosis. This sometimes helps differentiate between efficacies of various stent systems.

Nine samples of each Arm stent were implanted, one for each coronary artery. 24 hr release data in porcine serum were gathered. 3, 7 and 28 day in vivo release data were gathered (from the mammary arteries), as was 28 day quantitative coronary angioplasty (QCA), histology and morphometry.

In this study, 12 mm Vision Small stents (available from Guidant) were used. All drug solutions were sprayed in a 2% Solef™ in acetone/cyclohexanone formulation. All stents had a 100 μg PBMA primer. Table 1 shows the coating design of the stents used in this study.

TABLE 1

Coating design

| | Drug (D) | Polymer (P) | D:P | Drug % | Everolimus Target (μg) | Clobetasol Target (μg) | Solid Target (μg) |
|---|---|---|---|---|---|---|---|
| Arm 1 | Everolimus | Solef™ | 1:3 | 25.0 | 105 | — | 420 |
| Arm 2 | Clobetasol | Solef™ | 1:4.2 | 19.2 | — | 185 | 962 |
| Arm 3 | Ever & Clob | Solef™ | 1:3.49 | 22.2 | 105 | 80 | 833 |

The release rate data are shown in Table 2. As can be seen from Table 2, a coating based on Solef™ is capable of simultaneous release of both everolimus and clobetasol.

TABLE 2

Release rate data

| Arm | In vivo Day 3 % Clobetasol Release (n = 2) | In vivo Day 7 % Clobetasol Release (n = 3) | In vivo Day 28 % Clobetasol Release (n = 4) | In vitro 24 hr % Clobetasol Release in PS (n = 3) | In vivo Day 3 % Everolimus Release (n = 2) | In vivo Day 7 % Everolimus Release (n = 3) | In vivo Day 28 % Everolimus Release (n = 4) | In vitro 24 hr % Everolimus Release in PS (n = 3) |
|---|---|---|---|---|---|---|---|---|
| 1—Everolimus | | | | | 37.6% | 49.3% | 66.7% | 30.0% |
| 2—Clobetasol | 32.5% | 43.1% | 60.6% | 26.7% | | | | |

TABLE 2-continued

| | Release rate data | | | | | | | |
|---|---|---|---|---|---|---|---|---|
| Arm | In vivo Day 3 % Clobetasol Release (n = 2) | In vivo Day 7 % Clobetasol Release (n = 3) | In vivo Day 28 % Clobetasol Release (n = 4) | In vitro 24 hr % Clobetasol Release in PS (n = 3) | In vivo Day 3 % Everolimus Release (n = 2) | In vivo Day 7 % Everolimus Release (n = 3) | In vivo Day 28 % Everolimus Release (n = 4) | In vitro 24 hr % Everolimus Release in PS (n = 3) |
| 3—Everolimus + Clobetasol | 40.9% | 50.2% | 71.9% | 30.1% | 35.1% | 43.6% | 60.4% | 24.8% |

Figure 5:
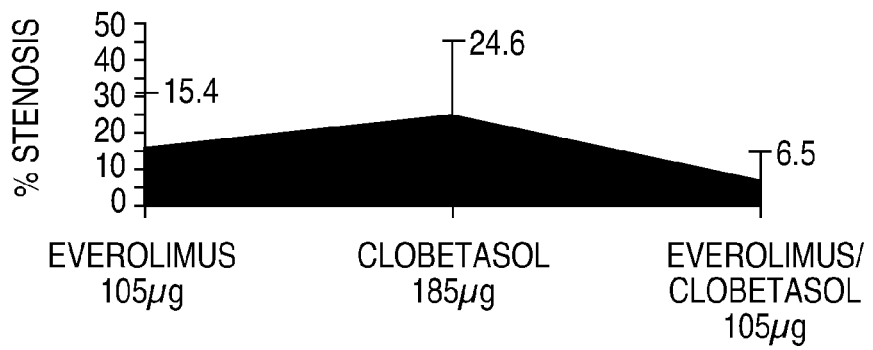
FIG. 5 shows the results of 28 day quantitative coronary angioplasty (QCA) of a porcine implant study on drug-delivery systems described herein.
Figure 7:
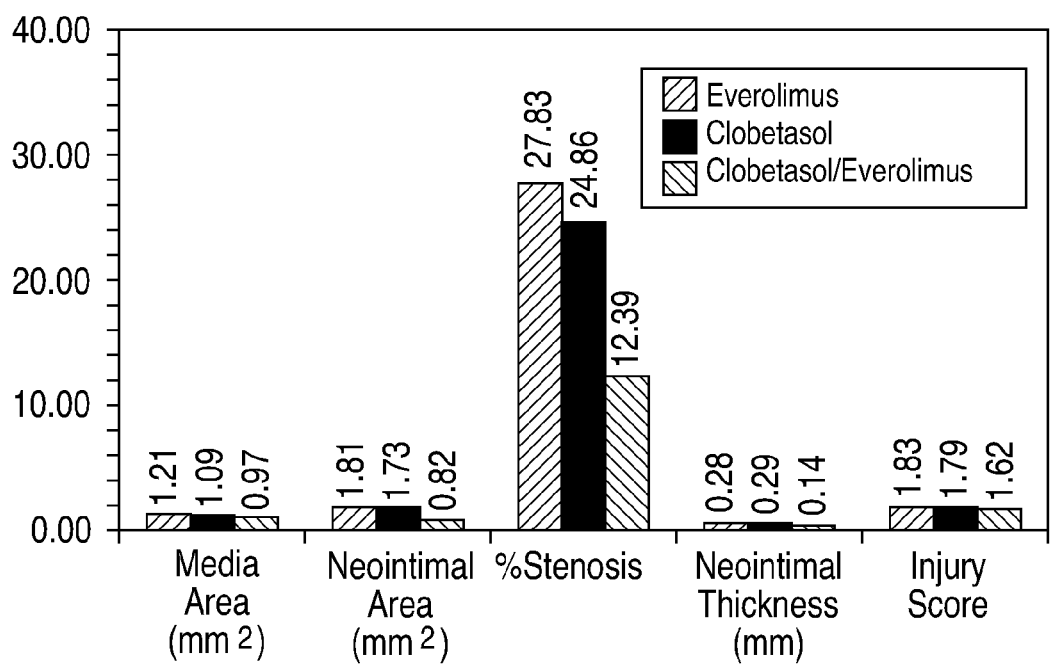
FIG. 7 shows the 28 day morphometry data of a porcine implant study on drug-delivery systems described herein.
Figure 6:
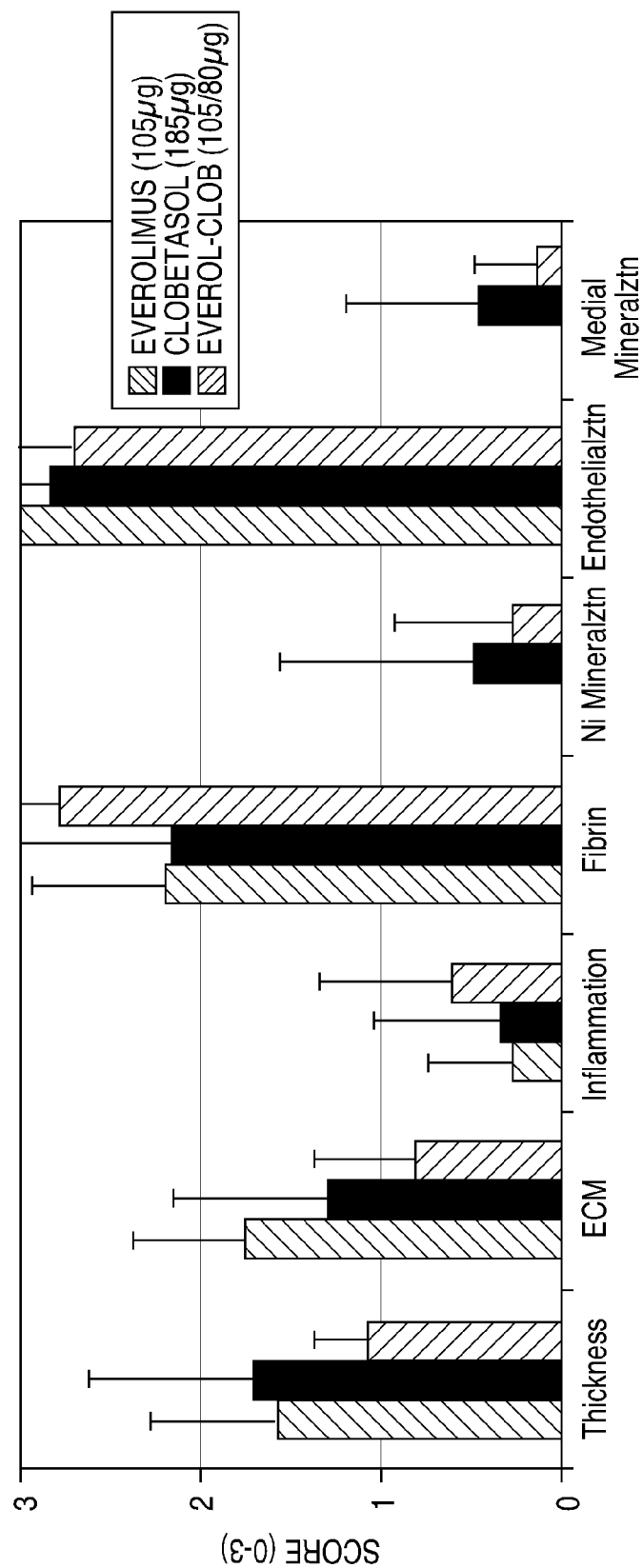
FIG. 6 shows 28 day histology data of a porcine implant study on drug-delivery systems described herein.

The results of 28 day QCA are shown in FIG. 5, the 28 day histology data are in FIG. 6, and the 28 day morphometry data are shown in FIG. 7 and summarized in Table 3 below.

Neointimal Area is the total amount of neointima as measured by a cross-sectional vessel section. This is essentially the area inside the Internal Elastic Lamina (IEL) minus the total area of the vessel lumen. Neointima refers to the new intimal growth that forms after stenting which resides between the IEL and the vessel lumen. Neointimal Thickness is the average distance between the IEL and the lumen. This is essentially the average thickness of the new intima that grows inside the stent after stenting.

Injury Score is a standardized scoring system that scores the amount of injury created in the vessel by the stent implantation. Currently, we use a range of 0 to 4 where 0 is no injury and 4 is the highest injury. There are specific quantitative and qualitative criteria for assigning a given score to a vessel.

Example 2

Porcine Implant Study

Described in this example is a 28 day porcine implant study that compared an everolimus-only stent, an everolimus-clobetasol combination drug delivery stent, and a clobetasol-only stent. The drugs were dispersed in a Solef polymer matrix, available from Solvay Solexis PVDF, Thorofare, N.J. The study was performed using three different drug delivery stents, Arm 1, Arm 2, and Arm 3. Arm 1 is Lemans stent (a stent available from Guidant based on PVDF-co-HFP) that included 64 μg everolimus with a drug-polymer ratio of 1:4.9, which was used as a control. Arm 2 is loaded with 64 μg everolimus and 32 μg clobetasol with a drug-polymer ratio of 1:4. Arm 3 was loaded with 32 μg clobetasol only with a drug-ratio of 1:4, with no everolimus. Table 5 shows the coating design of the stents used in this study.

The Arm 1, Arm 2, and Arm 3 stents were implanted in a 30% overstretch model. Nine samples of each Arm stent were implanted, one for each coronary artery. 24 hr release data in porcine serum were gathered. 3, 7 and 28 day in vivo release data were gathered (from the mammary arteries), as was 28 day quantitative coronary angioplasty (QCA), histology and morphometry. 28 day QCA, histology, and morphometry were collected from coronary arteries.

TABLE 3

| | 28 Day morphometry data from FIG. 7 | | | | | | | | |
|---|---|---|---|---|---|---|---|---|---|
| | AVERAGE | | | | | STANDARD DEVIATION | | | |
| | Media Area (mm^2) | Neointimal Area (mm^2) | % Stenosis | Neointimal Thickness (mm) | Injury Score | Media Area (mm^2) | Neointimal Area (mm^2) | % Stenosis | Neointimal Thickness (mm) | Injury Score |
| Everolimus | 1.21 | 1.81 | 27.83 | 0.28 | 1.83 | 0.23 | 0.72 | 13.18 | 0.11 | 0.23 |
| Clobetasol | 1.09 | 1.73 | 24.86 | 0.29 | 1.79 | 0.18 | 1.57 | 23.27 | 0.23 | 0.22 |
| Clobetasol/ Everolimus | 0.97 | 0.82 | 12.39 | 0.14 | 1.62 | 0.18 | 0.39 | 7.54 | 0.04 | 0.29 |

The p values from a t-test of the data from FIG. 7 are summarized in Table 4.

A "t-test" returns the probability associated with a Student's t-Test that determines whether two samples are likely to have come from the same two underlying populations that have the same mean. The value returned from the test, "p", is the probability that the two groups of data come from the same population. p Values less than or equal to 0.10 or 0.05 are generally considered significant (Zar, J H. *Biostatistical Analysis*. Englewood Cliffs, N.J.: Prentice-Hall Inc, 1974. pp 101-108).

TABLE 4

| | p Values from a t-test of the data from FIG. 7 | | | | |
|---|---|---|---|---|---|
| Arm Comparison | | Media Area | Neointimal Area | % Stenosis | Neointimal Thickness | Injury Score |
| EVER | COMBO | 0.05 | 0.01 | 0.02 | 0.01 | 0.18 |
| EVER | CLOB | 0.29 | 0.90 | 0.77 | 0.93 | 0.78 |
| COMBO | CLOB | 0.24 | 0.18 | 0.22 | 0.14 | 0.25 |

In this study, 12 mm Vision Small stents (available from Guidant) were used. All drug solutions were sprayed in a 2% Solef™ in acetone/cyclohexanone formulation. All stents had a 100 µg PBMA primer.

TABLE 5

Coating design

| | Drug (D) | Polymer (P) | D:P | Drug % | Everolimus Target (µg) | Clobetasol Target (µg) | Solid Target (µg) |
|---|---|---|---|---|---|---|---|
| Arm 1 | Everolimus | Solef™ | 1:4.9 | 17.0 | 64 | — | 375 |
| Arm 2 | Ever & Clob | Solef™ | 1:4 | 20.0 | 64 | 32 | 480 |
| Arm 3 | Clobetasol | Solef™ | 1:9 | 10.0 | — | 32 | 320 |

The release rate data are shown in Table 6. As can be seen from Table 6, a coating based on Solef™ is capable of simultaneous release of both everolimus and clobetasol.

TABLE 6

Release rate data

| Arm | In Vitro 24 hr % Clobetasol Release in PS (n = 3) | In Vivo Day 1 % Clobetasol Release (n = 4) | In Vivo Day 3 % Clobetasol Release (n = 4) | In Vivo Day 7 % Clobetasol Release (n = 4) | In Vivo Day 28 % Clobetasol Release (n = 3) | In Vitro 24 hr % Everolimus Release in PS (n = 3) | In Vivo Day 1 % Everolimus Release (n = 4) | In Vivo Day 3 % Everolimus Release (n = 4) | In Vivo Day 7 % Everolimus Release (n = 4) | In Vivo Day 28 % Everolimus Release (n = 3) |
|---|---|---|---|---|---|---|---|---|---|---|
| 1—Everolimus | — | — | — | — | — | 30.4% | 33.1% | 45.6% | 62.2% | 82.9% |
| 2—Everolimus + Clobetasol | 35.1% | 33.9% | 45.8% | 55.4% | 81.2% | 28.4% | 31.9% | 40.0% | 48.3% | 71.1% |
| 3—Clobetasol | 34.2% | 33.9% | 48.0% | 60.5% | 85.0% | — | — | — | — | — |

Figure 8:
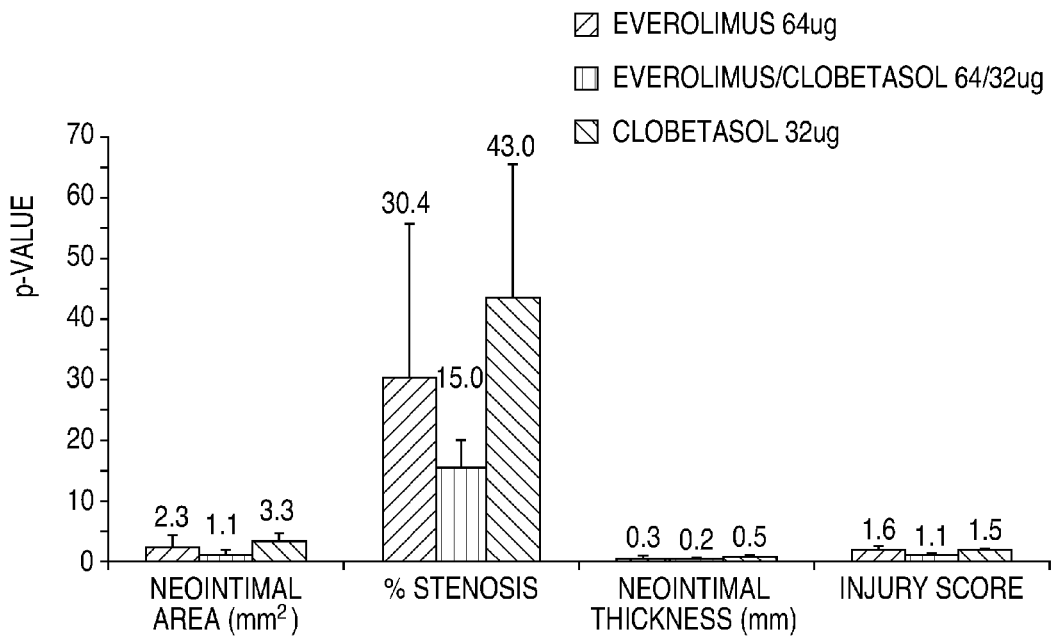
FIG. 8 shows the results of 28 day quantitative coronary angioplasty (QCA) of a porcine implant study on drug-delivery systems described herein.

The results of the 28 day morphometry data are shown in FIG. 8 and summarized in Table 7 below.

TABLE 7

28 Day morphometry data from FIG. 8

| | | Media Area (mm^2) | Neointimal Area (mm^2) | % Stenosis | Neointimal Thickness (mm) | Injury Score |
|---|---|---|---|---|---|---|
| Ever 64 ug | Average | 1.22 | 2.30 | 30.38 | 0.34 | 1.64 |
| | Standard Deviation | 0.26 | 2.06 | 25.32 | 0.33 | 0.59 |
| Ev/Cl 64/32 ug | Average | 0.92 | 1.10 | 14.99 | 0.23 | 1.07 |
| | Standard Deviation | 0.26 | 0.34 | 4.93 | 0.19 | 0.29 |
| Clob 32 ug | Average | 1.21 | 3.26 | 43.04 | 0.46 | 1.47 |
| | Standard Deviation | 0.12 | 1.54 | 22.13 | 0.23 | 0.30 |

The p values from a t-test of the data from FIG. 8 are summarized in Table 8.

TABLE 8 p Values from a t-test of the data from FIG. 8

| Arm Comparison | | Neointimal Area (mm²) | % Stenosis | Neointimal Thickness (mm) | Injury Score |
|---|---|---|---|---|---|
| Ever | Combo | 0.15 | 0.13 | 0.41 | 0.03 |
| Ever | Clob | 0.36 | 0.37 | 0.46 | 0.49 |
| Combo | Clob | 0.03 | 0.05 | 0.09 | 0.04 |

Figure 9:
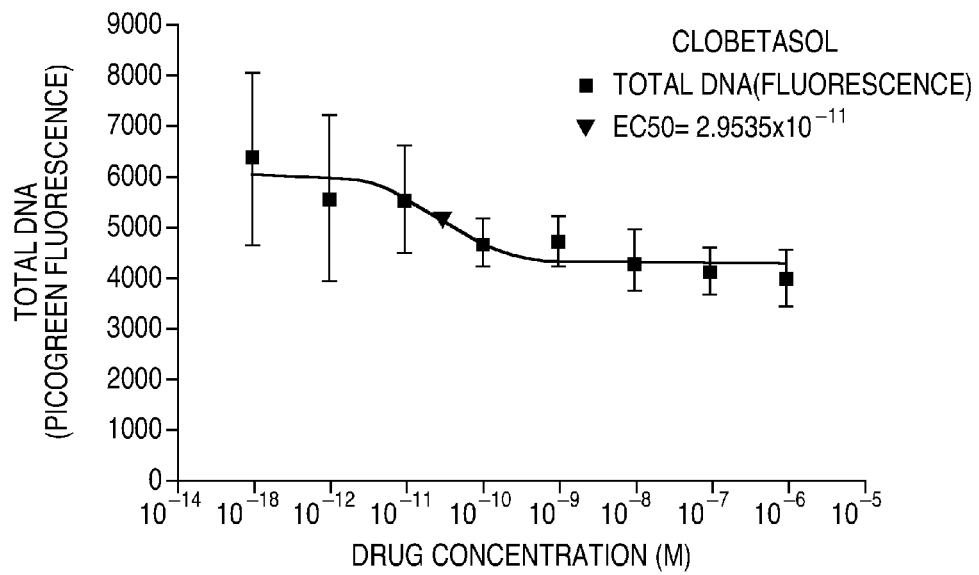
FIG. 9 depicts a proliferation assay that shows a dose dependent inhibition of vascular smooth muscle proliferation.

Clobetasol is non-toxic even at the highest concentrations typically tested in cell culture ($10^{-6}$ M). FIG. 9 depicts a proliferation assay that shows a dose dependent inhibition of vascular smooth muscle proliferation and a low EC50 value of $3 \times 10^{-11}$ M. The Efficacy of the drug is 25%.

A proliferation assay is a cell culture assay in which smooth muscle cells are exposed to various concentrations of a given drug. The y-axis is a measure of the total number of DNA strands or cell nuclei. If cells are dividing (proliferating), the amount of DNA increases. EC50 is the concentration of drug that causes half the total effect. For example, if the greatest amount of proliferation reduction is 60% reduction as compared to no drug, then the EC50 is the concentration of drug that causes a 30% reduction in proliferation. Efficacy refers to the effectiveness of the drug in preventing proliferation of smooth muscle cells.

Figure 10:
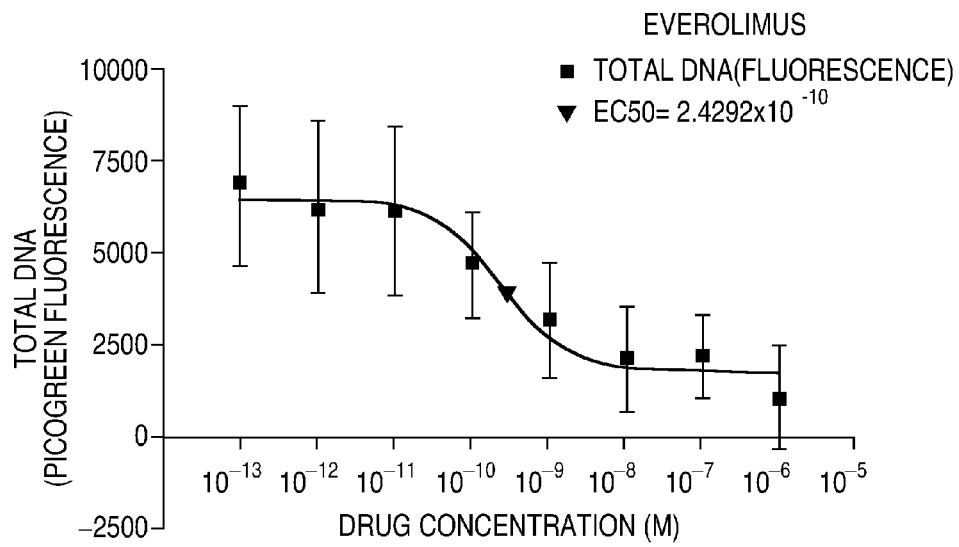
FIG. 10 depicts a proliferation assay with Everolimus which also shows inhibition of vascular smooth muscle proliferation.

FIG. 10 depicts a proliferation assay with Everolimus only, which also shows inhibition of vascular smooth muscle proliferation. The Efficacy of the drug is 62%.

Figure 11:
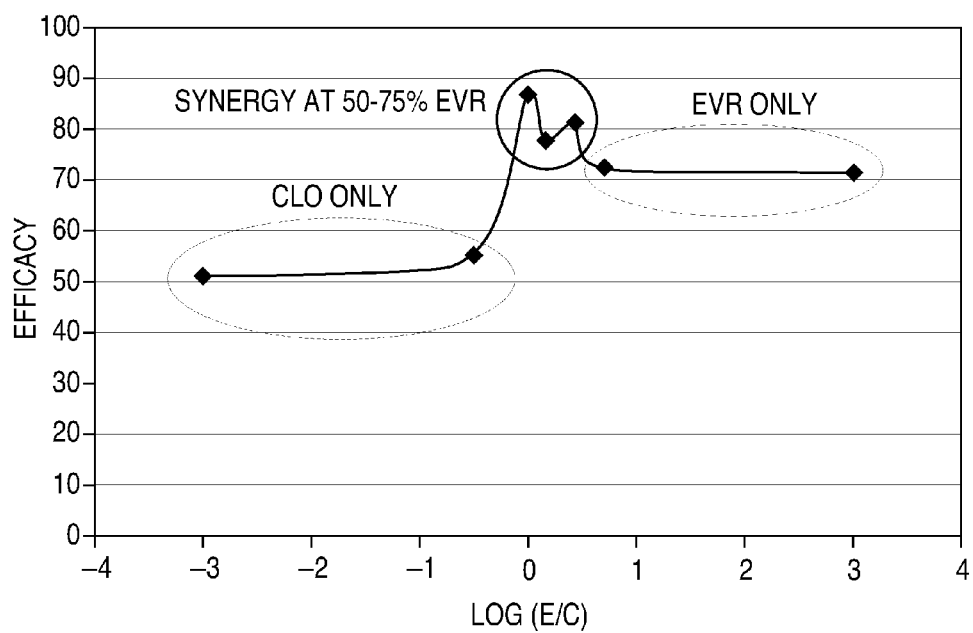
FIG. 11 depicts results of a proliferation assay with varying ratios of everolimus and clobetasol.

FIG. 11 depicts results of a proliferation assay with varying ratios of everolimus and clobetasol. FIG. 11 illustrates a plot of the efficacy of inhibition of vascular smooth muscle proliferation versus the logarithm of the everolimus-clobetasol ratio. The circled portion of the curve in FIG. 11 shows that everolimus and clobetasol have a synergistic effect that results in a higher efficacy within a range of the ratio of the two drugs.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of treating restenosis or vulnerable plaque of a blood vessel comprising:
    implanting a stent in a blood vessel of a patient, wherein the stent comprises a scaffolding structure made of a bioabsorbable polymer, wherein an effective amount of a steroidal anti-inflammatory agent or a non steroidal anti-inflammatory agent is mixed or dispersed throughout the scaffolding structure;
    administering to the patient an effective amount of an anti-proliferative agent; and
    allowing the effective amount of the steroidal anti-inflammatory agent or the non steroidal anti-inflammatory agent to elute to the blood vessel from the scaffolding structure;
    wherein the combination of the anti-proliferative and anti-inflammatory agents is for treatment of restenosis or vulnerable plaque.

2. The method of claim 1, wherein the scaffolding structure allows for sustained release of the steroidal anti-inflammatory agent or the non steroidal inflammatory agent throughout the degradation process of the scaffolding structure since the agent elutes as the scaffolding structure erodes.

3. The method of claim 1, wherein the anti-proliferative agent is everolimus and the steroidal or non-steroidal anti-inflammatory agent is clobetasol.

4. The method of claim 3, wherein the ratio of the dose of everolimus to the dose of clobetasol is 1:1 to 3:1 on a molar basis.

5. The method of claim 1, wherein the effective amount of the anti-proliferative agent is administered locally by a means other than a stent.

6. The method of claim 5, wherein local administration is administration by a catheter, administration by direct injection, administration by an implant, or a combination thereof.

7. The method of claim 1, wherein the effective amount of the anti-proliferative agent is administered systemically.

8. The method of claim 7, wherein the systemic administration is oral administration, parenteral administration, or a combination thereof.

9. The method of claim 8, wherein the parenteral administration is intravascularly, rectally, intranasally, intrabronchially, transdermally, or a combination thereof.

* * * * *